United States Patent [19]

Timmler et al.

[11] 3,979,204

[45] Sept. 7, 1976

[54] PLANT GROWTH REGULANT COMPOSITIONS COMPRISING 2-CYANO-BICYCLO[2,2,1]HEPTANE

[75] Inventors: Helmut Timmler, Wuppertal; Klaus Lürssen, Koenigsdorf, both of Germany

[73] Assignee: Bayer Aktiengesellschaft, Leverkusen, Germany

[22] Filed: Dec. 16, 1974

[21] Appl. No.: 533,392

[30] Foreign Application Priority Data

Jan. 5, 1974 Germany............................ 2400454

[52] U.S. Cl........................................ 71/105; 71/76
[51] Int. Cl.²................................................ A01N 9/20
[58] Field of Search ........................................ 71/105

[56] References Cited
UNITED STATES PATENTS

| 2,759,011 | 8/1956 | Soloway | 71/105 |
| 3,629,315 | 12/1971 | Pews | 71/105 |

OTHER PUBLICATIONS

Journal of American Chemical Society, 93, 1971, 5896–5897.

*Primary Examiner*—Joseph P. Brust
*Attorney, Agent, or Firm*—Burgess, Dinklage & Sprung

[57] ABSTRACT

Plant growth regulant compositions containing as an active ingredient 2-cyano-bicyclo[2,2,1]heptane exhibit strong growth regulating activity, e.g., to induce shortening and thickening of the stem in cereals and other crop plants, increasing the yields of certain crops, or the setting of fruit.

9 Claims, No Drawings

PLANT GROWTH REGULANT COMPOSITIONS COMPRISING 2-CYANO-BICYCLO[2,2,1]HEPTANE

The present invention relates to plant-growth regulatory compositions containing, and to a method for regulating plant growth using, 2-cyanobicyclo[2,2,1]heptane.

It is known that (2-chloroethyl)-trimethylammonium chloride can be used for influencing plant growth. Thus, for example, a shortening and thickening of the stem in cereals and other crop plants can be achieved with the aid of (2-chloroethyl)-trimethylammonium chloride (see U.S. Pat. Nos. Specs. 3,318,910; 3,280,136; 3,264,317 and 3,270,027). However, the action of this compound is not always entirely satisfactory, especially if low amounts and low concentrations are used.

It has now been found that 2-cyano-bicyclo-[2,2,1]heptane of the formula

 (I)

exhibits very good plant-growth-regulating properties.

The present invention therefore provides a plant-growth-regulating composition containing as active ingredient the compound of the formula (I) in admixture with a solid or liquefied gaseous diluent or carrier or in admixture with a liquid diluent or carrier containing a surface-active agent.

The present invention also provides a method of regulating the growth of plants, which comprises applying to the plants or a plant habitat the compound of the formula (I) alone or in the form of a composition containing as active ingredient the compound of the formula (I) in admixture with a diluent or carrier.

Surprisingly, 2-cyano-bicyclo[2,2,1]heptane shows a substantially stronger growth-regulating activity than the known compound (2-chloroethyl)-trimethylammonium chloride, which is the nearest active compound of the same type of action. The compound which can be used according to the invention thus represents a valuable enrichment of the art.

2-Cyano-bicyclo[2,2,1]heptane, which can be used according to the invention, is known per se (see Journal of American Chemical Society, 93 (1971) 5896–5897). However, the use of the compound of the formula (I) for regulating plant growth is new as are plant-growth regulating compositions containing it.

2-Cyano-bicyclo[2,2,1]heptane can be prepared, for example, by hydrogenating 2-cyano-bicyclo[2,2,1]heptene-5 in methanol solution in the presence of Raney nickel and with addition of iron (II) sulphate, at slightly elevated temperatures under a pressure of 50 to 60 atmospheres. To isolate the product, the reaction mixture is filtered and concentrated by distilling off the solvent. The residue which hereupon remains is subjected to a vacuum distillation.

The active compound which can be used according to the invention affects the physiological metabolism of plant growth and can therefore be used as a plant-growth regulator.

The various effects of the active compound depend essentially on the time at which it is used, relative to the stage of development of the seed or of the plant, and on the concentrations used.

Plant-growth regulators are used for various purposes which are related to the stage of development of the plant.

The growth of the plants can be greatly inhibited by means of the active compound used according to the invention. This inhibition of growth is of commercial interest, for example, in the case of grasses, since if the growth of grass can be repressed the frequency of cutting the grass (for instance, mowing the lawn) can be reduced. An inhibition of vegetative growth is also of great importance in the case of cereals, since it makes it possible to reduce or completely prevent lodging.

In the case of many crop plants, inhibition of the vegetative growth permits denser planting of the crop so that a greater yield per area of ground can be achieved.

A further mechanism of increasing the yield by means of growth inhibitors is based on the fact that the nutrients benefit blossoming and fruit formation to a greater extent while vegetative growth is restricted.

Promotion of vegetative growth can also be achieved with the growth regulator according to the invention. This is of great utility if it is the vegetative parts of the plants which are harvested. Promoting the vegetative growth can, however, also simultaneously lead to a promotion of generative growth so that, for example, more fruit, or larger fruit, is formed.

Increases in yield can also be achieved by affecting the plant metabolism without changes in vegetative growth becoming noticeable.

Parthenocarpous fruit can be formed under the influence of growth regulators. Furthermore, the gender of the flowers can be influenced.

Using growth regulators, it is also possible favorably to influence the production or efflux of secondary plant materials. The stimulation of latex flow in rubber trees may be mentioned as an example.

During the growth of the plant, lateral branching can be increased by chemical breaking of the apical dominance. There is interest in this, for example, in the case of plant propagation by cuttings. However, depending on the concentration, it is also possible to inhibit the growth of side shoots, for example to prevent the formation of side shoots in tobacco plants after decapitation and thus to promote leaf growth.

Under certain conditions, premature shedding of fruit can be prevented or shedding of fruit assisted, in the sense of a chemical thinning-out, up to a certain degree. However, assisting the shedding of fruit can also be utilized by carrying out the treatment at harvest time, which facilitates harvesting.

Using growth regulators it is furthermore possible to accelerate or delay the ripening of fruit and to improve the coloring of fruit. Concentrating the ripening of fruit within a certain period of time is also possible. The desired effects can be achieved by varying the concentrations of the active compound and by application at various times during the development of the plant.

Using growth regulators, frost resistance and drought resistance can be induced in plants.

The latent period of seeds or buds of plants, that is to say the endogenic annual rhythm, can be influenced by the active compound, so that the plants, for example, germinate, shoot or blossom t a time at which they normally show no readiness to do so.

Using a growth-regulating active compound it is also possible to delay the shooting of buds or the germination of seeds, for example, to avoid damage by late frosts in regions where frost is a hazard.

The active compound to be used according to the present invention can be converted into the usual formulations, such as solutions, emulsions, suspensions, powders, pastes and granulates. These may be produced in known manner, for example by mixing the active compound with extenders, that is liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxy-ethylene-fatty acid esters, polyoxyethylene-fatty alcohol ethers, for example alkylarylpolyglycol ethers, alkyl sulphonates, alkyl sulphates and aryl sulphonates as well as albumin hydrolyzation products; and preferred examples of dispersing agents include lignin sulphite waste liquors and methyl cellulose.

The active compound of the formula (I) can be present in the formations as a mixture with other active compounds.

The formulations in general contain from 0.1 to 95% by weight of active compound, preferably from 0.5 to 90% by weight.

The active compound can be used as such, in the form of its formulations or in the use forms prepared therefrom, such as ready-to-use solutions, emulsifiable concentrates, emulsions, foams, suspensions, wettable powders, pastes, soluble powders, dusting agents and granules. It may be used in the customary manner, for example by watering, spraying, atomizing, scattering, dusting or treatment of seed.

The active-compound concentrations can be varied within a fairly wide range. In general, concentrations of 0.0005 to 2% by weight, preferably of 0.01 to 0.5% by weight, are used.

Furthermore, 0.01 to 10 kg, preferably 0.05 to 5 kg, of active compound are in general employed per hectare of ground.

The preferred period of time within which the growth regulator is employed depends on the climatic and vegetative circumstances.

The present invention further provides plants of which the growth has been regulated by their being grown in areas in which immediately prior to and/or during the time of the growing the compound of the formula (I) was applied alone or in admixture with a diluent or carrier.

The Examples which follow show the activity of the compound which can be used according to the invention as a growth regulator and are illustrative. Thus, this does not imply excluding the possibility of further applications as a growth regulator.

EXAMPLE A

Increase in yield/bush beans

| Solvent: | 10 parts by weight of methanol |
| Emulsifier: | 2 parts by weight of polyethylene-sorbitan monolaurate |

To produce a suitable preparation of active compound, 1 part by weight of active compound was mixed with the stated amounts of solvent and emulsifier and made up to the desired concentration with water.

Groups of 4 bean plants (*Phaseolus vulgaris*) were grown in 14 pots. When flowering started, the plants were sprayed with a total of 400 ml of an active-compound preparation. After 3 weeks' growth in a greenhouse, the number of pods and the weight of the pods per pot was determined. The results were tested for significance by the t-test, according to Student.

The active compound concentrations and results can be seen for the table which follows:

Table A

| Active compound | | Increase in yield/bush beans | |
|---|---|---|---|
| | Concentration % | Number of pods in % of the control | Total weight of the pods in % of the control |
| Water (control) | 0 | =100 | =100 |
| (I) benzyl cyanide structure | 0.025 | 113 | 131 |
| | 0.05 | 105 | 135* |
| | 0.1 | 105 | 121 |

*statistically reliable at p = 0.05 (p = probability)

It can be seen from the figures listed in the table that both the number and the weight of the pods are in part significantly higher in the case of the plants treated with active compound than in the untreated control plants.

EXAMPLE B

Influence on growth/cress seedlings

| Solvent: | 10 parts by weight of methanol |
|---|---|
| Emulsifier: | 2 parts by weight of polyethylene-sorbitan monolaurate |

To produce a suitable preparation of active compound, 1 part by weight of active compound was mixed with the stated amounts of solvent and emulsifier and made up with water to the desired concentration.

Groups of 50 cress seeds were placed on a stiff filter paper cut to a rectangular shape, which was impregnated with an 0.02% strength solution of the particular preparation of active compound. The seeds adhered so firmly to the moist filter paper that they did not fall off even when the paper was stood upright. The moist filter paper carrying the seeds was placed vertically in a beaker (diameter about 7 cm) which contained 25 ml of an 0.02% strength solution of active compound. The beaker was covered with a glass disc. After 5 days, the length of the shoot and roots was determined, and the inhibition of growth compared to the untreated control plants was expressed in %. 100% denotes cessation of growth and 0% denotes a growth which corresponded to that of the untreated control plants. In addition, the hairiness of the roots of all test plants was assessed qualitatively.

The active compounds, active-compound concentrations and results can be seen from the table which follows:

Table B

| Active compound | Influence on growth/cress seedlings Concentration in % | Inhibition of growth (in %) Shoot | Root | Hairiness of root |
|---|---|---|---|---|
| Water (control) | 0 | 0 | 0 | normal |
| $Cl-CH_2-CH_2-N^+(CH_3)_3Cl^-$ (known) | 0.02 | 0 | 0 | normal |
|  (I) | 0.02 | 40 | 40 | conspicuously pronounced |

EXAMPLE C

Increase in setting of fruit/apples

| Solvent: | 10 parts by weight of methanol |
|---|---|
| Emulsifier: | 2 parts by weight of polyethylene-sorbitan monolaurate |

To produce a suitable preparation of active compound, 1 part by weight of active compound was mixed with the stated amounts of solvent and emulsifier and made up with water to the desired concentration.

In an orchard, branches, each carrying about 30 blossoms, of apple trees (Jonathan variety) were sprayed, 3 days after coming into full blossom, in 5 repeats, with an active-compound preparation of a given concentration. The exact number of blossoms was determined for each branch. After the June drop, the fruit per branch were counted. The percentage setting of fruit — that is to say the number of fruit expressed in % of the number of blossoms — was calculated. In addition, the % by which the setting of fruit was greater in the case of the branches treated with active compound than in the case of the untreated branches was determined. The setting of fruit of the untreated control branches was here taken as 100%.

The active compound concentrations and results can be seen from the table which follows:

Table C

| Active compound | | Increase in setting of fruit/apples Concentration in % | Percentage setting of fruit | Setting of fruit in % of the control |
|---|---|---|---|---|
| Water (control) | | 0 | 14.5 | =100 |
|  | (I) | 0.005 | 25.9 | 179 |
| | | 0.020 | 24.6 | 170 |
| | | 0.100 | 22.0 | 152 |

It can be seen from the figures listed in the table that the branches treated with active compound show distinctly higher setting of fruit than corresponding untreated branches.

The preparation of the active known compound is illustrated in the following Example:

Example 1 — Preparation of
2-Cyano-bicyclo[2,2,1]heptane

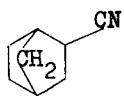 (I)

305 g (2.6 moles) of 2-cyano-bicyclo[2,2,1]heptane-5 in 1.5 l of methanol were hydrogenated in the presence of 30 g of Raney nickel and with the addition of 45 ml of a 0.1 molar ferrous sulphate solution at 35° to 40°C. under a pressure of 50 to 60 atmospheres. After cooling to room temperature, the reaction mixture was filtered to remove the nickel catalyst. The filtrate was then concentrated by distilling off the solvent. The residue which hereupon remained was distilled under reduced pressure. This gave 262 g (85% of theory) of 2-cyano-bicyclo[2,2,1]heptane of boiling point 88°C/17 mm Hg.

The starting material was prepared as follows:

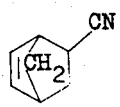

159 g (3 moles) of acrylonitrile were dissolved in 100 ml of benzene and warmed to 50°C. after adding a pinch of hydroquinone. 196 g (3 moles) of cyclopentadiene were added dropwise at this temperature, with intensive stirring. In the course thereof, the temperature of the reaction mixture rose (it should not exceed 70°C.). After the exothermic reaction had subsided, the mixture was stirred for 1 hour at 80°C. The solvent was then distilled off and the residue was rectified in vacuo. This gave 272 g (76% of theory) of 2-cyano-bicyclo[2,2,1]heptene-5 of boiling point 82°–87°C/15 mm Hg.

It will be understood that the foregoing specification and examples are illustrative but not limitative of the present invention inasmuch as other embodiments within the spirit and scope of the invention will suggest themselves to those skilled in the art.

What is claimed is:

1. Plant growth regulating composition which consists essentially of a carrier selected from the group consisting of (1) a ground natural mineral or a ground synthetic mineral solid carrier containing a surface-active agent selected from the group consisting of non-ionic and anionic emulsifiers, dispersants and foam forming agents and mixtures of such agents and (2) a liquid carrier selected from the group consisting of aromatic hydrocarbons, chlorinated aromatic or aliphatic hydrocarbons, aliphatic hydrocarbons, ethers, esters, ketones, strongly polar solvents and water and containing a surface-active agent selected from the group consisting of a non-ionic and anionic emulsifiers, dispersants and foam-forming agents, and mixtures of such agents, and a 2-cyano-bicyclo[2,2,1]heptane of the formula

comprising from 0.1 to 95% by weight of the total composition and in amount sufficient to increase the yield of crop plants.

2. Plant growth regulating compositions in a ready-to-use formulation selected from the group consisting of ready-to-use solutions, emulsifiable concentrates, emulsions, foams, suspensions, wettable powders, pastes, soluble powders, dusting agents and granules wherein the active ingredient is 2-cyano-bicyclo[2,2,1]heptane and constitutes from 0.0005 to 2% by weight of such ready-to-use formulation in an amount sufficient to increase the yield of crop plants.

3. Composition as claimed in claim 1 wherein the said active ingredient constitutes from 0.5 to 90% of the total composition.

4. Method of increasing the yield of crop plants which method comprises applying effective amounts of 2-cyano-bicyclo[2,2,1]heptane to at least one of a locus selected from the plants themselves and the habitat of the plants.

5. Method as claimed in claim 4 wherein said compound is applied in the form of a composition containing from 0.005 to 2% of the active compound by weight.

6. Method as claimed in claim 5 wherein the content of active compound in the composition is 0.01 to 0.5%.

7. Method as claimed in claim 4 wherein said compound is applied to an area of agriculture in an amount of 0.01 to 10 kg per hectare.

8. Method as claimed in claim 7 wherein the amount of 0.05 to 5 kg per hectare.

9. Method as claimed in claim 4 wherein the compound is applied to increase the setting of fruit on fruit trees.

* * * * *